(12) United States Patent
Kidani et al.

(10) Patent No.: US 7,440,545 B2
(45) Date of Patent: Oct. 21, 2008

(54) POSITIONING SYSTEM AND METHOD FOR RADIATION THERAPY

(75) Inventors: Takao Kidani, Hitachi (JP); Masahiro Hosaka, Hitachi (JP); Yoshihiko Nagamine, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 43 days.

(21) Appl. No.: 11/512,316

(22) Filed: Aug. 30, 2006

(65) Prior Publication Data
US 2007/0053492 A1 Mar. 8, 2007

(30) Foreign Application Priority Data
Aug. 31, 2005 (JP) ............................. 2005-252607

(51) Int. Cl.
*A61N 5/10* (2006.01)
(52) U.S. Cl. ............................. 378/65; 378/20; 378/147
(58) Field of Classification Search .................... 378/4, 378/20, 51, 62, 64, 65, 91, 98, 98.2, 98.6, 378/145, 147, 150, 151, 193, 195, 205, 208, 378/209
See application file for complete search history.

(56) References Cited
U.S. PATENT DOCUMENTS
2003/0202632 A1* 10/2003 Svatos et al. .................. 378/65

FOREIGN PATENT DOCUMENTS

| JP | 04-058266 | 2/1992 |
|---|---|---|
| JP | 2000-510023 | 8/2000 |
| JP | 2004-267250 | 9/2004 |
| JP | 2005-071291 | 3/2005 |
| JP | 2005-253755 | 9/2005 |
| WO | WO98/18523 | 5/1998 |

* cited by examiner

*Primary Examiner*—Courtney Thomas
(74) *Attorney, Agent, or Firm*—Mattingly, Stanger, Malur & Brundidge, PC

(57) ABSTRACT

A positioning system for radiation therapy comprises a patient positioner drive unit for moving a patient positioner supporting a patient, a snout drive unit for rotating a snout including a collimator set therein, and a processing unit for controlling the snout drive unit and the patient positioner drive unit such that the positioning of the patient is performed by moving the patient positioner supporting the patient after the positioning of the collimator has been performed by rotating the snout including the collimator set therein. Exposure of the patient to X-rays irradiated for the positioning can be reduced.

24 Claims, 11 Drawing Sheets (b)

(a)

POSITIONING SYSTEM AND METHOD FOR RADIATION THERAPY

BACKGROUND OF THE INVENTION

1. Field of the Invention

The present invention relates to radiation therapy in which a radiation, such as an X-ray or a particle beam including a proton beam, is irradiated to a tumor for treatment. More particularly, the present invention relates to a positioning system and method for the radiation therapy, which is useful to perform positioning of a patient and a collimator.

2. Description of the Related Art

In radiation therapy, treatment is performed by irradiating a radiation to a tumor and damaging DNA of a tumor cell. It is therefore required to irradiate the radiation in a precise manner so that DNAs of normal cells near the tumor are not damaged. Particularly, in radiation therapy using a particle beam such as a proton beam, the beam can be concentrated to the tumor with a higher dose based on beam characteristics, whereas more accurate positioning is required. This leads to the necessity of deciding the position of the patient relative to the beam with high accuracy, and of forming radiation field as per planning.

Particle beam therapy is performed as per a treatment plan prepared in advance. However, a slight deviation occurs between the position of the tumor in the patient body and the planned setting position due to various factors. To realize positioning of the patient as per the treatment planning, therefore, it is required to precisely calculate the deviation between those two positions and to correct the position of a patient positioner by using a patient moving apparatus in accordance with the calculated deviation.

The positioning of the patient in a treatment room is first performed by making the patient fixed to an immobilization device on the patient positioner, and executing rough positioning with the aid of a body surface marker and a laser marker. Then, X-ray images of the patient are captured by using an image capturing system, e.g., two sets of X-ray equipment, in order to confirm the current patient position. Resulting X-ray images are called positioning images. The positioning images are transmitted to a positioning apparatus and are stored in a medical image server.

On a display screen of the positioning apparatus, a reference image calculated and stored in advance and the positioning image are displayed to calculate the deviation of the patient position through comparison between both the images. The calculation can be performed, for example, by a method of setting calculation points on landmarks (each landmark being selected as a location, e.g., a bone part, which is clearly recognizable) on both the images by an operator using a mouse, and calculating the deviation through comparison between coordinate values of the calculation points based on an approximation method, e.g., the least square method (see, e.g., Patent Document 1: JP,A 2000-510023 (FIGS. 6-7)), or a method of comparing pixel values of both the images and calculating the deviation based on an approximation method, e.g., the least square method, at which the sum of errors of the pixel values is minimized (see, e.g., Patent Document 2: JP,A 2004-267250 (FIGS. 8-12)).

The thus-calculated deviation (including the amount of parallel shift and the amount of rotation) is converted to a position deviation of the patient positioner through coordinate transform in the positioning apparatus and is transmitted to the patient moving apparatus. In accordance with the transmitted deviation, a patient positioner controller in the patient moving apparatus controls a patient positioner drive unit to move and/or rotate the patient positioner for correction of the position deviation, thereby completing the patient positioning.

In addition, to precisely produce the radiation field as per planning, positioning of a collimator that decides the radiation field is also required to be performed with high accuracy. Generally, the collimator is mounted in a snout rotatably mounted to a fore end of an irradiation nozzle (see, e.g., Patent Document 3: JP,U 4-58266 (FIG. 1)). It is therefore important to decide the rotational angle of the snout with high accuracy.

SUMMARY OF THE INVENTION

In the case using a particle beam, such as a proton beam, which has a Bragg Peak characteristic, more accurate positioning is required to effectively utilize high irradiation accuracy of the beam. To reduce unwanted irradiation to the patient, however, high-accurate positioning is required not only for the position of the patient, but also for the position of the snout in which is mounted the collimator for forming the radiation field.

Further, the reference image calculated in the treatment planning is not always matched with the positioning image obtained as an actual X-ray image. It is therefore important to consider the relationship between the tumor position and the radiation field when the positioning is performed.

The known patient positioning method has the following problems. When a sufficient contrast is not obtained in the positioning image, or when an extra object, e.g., an immobilization device, is additionally taken in the image, the calculation points cannot be precisely set. Also, because the calculation of the position deviation based on the comparison of pixel values cannot be applied, a variation may occur in the positioning accuracy.

Further, with the known method for correcting an error in the amount of snout rotation, because the operator visually judges the error in the amount of snout rotation, a possibility of causing a variation in error correction is not avoided, and reproducibility is not obtained at a satisfactory level.

Moreover, the known positioning system requires the positioning of the collimator to be performed after the patient positioning. On that occasion, an X-ray image of the patient is captured again by using the X-ray equipment in the state of the collimator being set. In other words, the patient is exposed to X-rays twice when the X-ray images are captured for the patient positioning and the collimator positioning. This leads to a problem that the exposure of the patient to X-rays is increased.

With the view of solving the above-mentioned problems in the related art, a first object of the present invention is to provide a positioning system and method for radiation therapy, which can reduce a variation in positioning accuracy, cut unwanted exposure of a patient to radiations, and increase the efficiency of positioning operations.

A second object of the present invention is to provide a positioning system and method for radiation therapy, which can reduce exposure of a patient to X-rays irradiated for positioning.

To achieve the above first object, the present invention is featured in displaying, on a reference image, figure data representing a planned collimator contour shape which indicates a radiation field and is registered in image information of the reference image during treatment planning, displaying the figure data representing the planned collimator contour shape in a display area in which is displayed a positioning image of a patient, and producing positioning information of a patient positioner based on a figure representing the planned collimator contour shape and the positioning image which are both displayed in that display area.

That feature is able to reduce a variation in positioning accuracy caused depending on conditions of the positioning image, such as a contrast, thus enabling the positioning operations to be precisely performed in consideration of the positional relationship between the tumor position and the radiation field.

To achieve the above first object, the present invention is also featured in displaying the figure data representing the planned collimator contour shape in a display area in which is displayed a positioning image of the collimator, and producing positioning information of the collimator based on the figure representing the planned collimator contour shape and the positioning image of the collimator which are both displayed in that display area.

With that feature, correction of an error in the amount of snout rotation can be performed with automatic adjustment based on image recognition while reducing a variation depending on individual operators, improving reproducibility, and cutting the operations to be performed by the operator.

To achieve the above first and second objects, the present invention is featured in comprising a patient positioner drive unit for moving a patient positioner supporting a patient; a snout drive unit for rotating a snout including a collimator set therein; and a processing control unit for producing first positioning information to control the snout drive unit such that the snout is rotated for the positioning of the collimator, and second positioning information to control the patient positioner drive unit such that the patient is moved for the positioning of the patient.

With that feature of the present invention, since the patient is immobilized on the patient positioner and the positioning of the patient is performed after performing the positioning of the collimator, the patient is avoided from being exposed to X-rays twice when X-ray images are captured for the positioning of the collimator and the positioning of the patient. Accordingly, the exposure of the patient to X-rays in the positioning process can be reduced.

Preferably, the present invention is featured in further comprising an image capturing device for capturing an image of a contour shape of the collimator in an irradiating direction of a radiation; and a display for displaying information of the captured image of said collimator in superimposed relation to figure data representing a collimator contour decided in treatment planning. In this case, the processing control unit produces the first positioning information used for the positioning of the collimator based on collimator contour position information captured in the image information of the collimator and collimator contour position information provided by the figure data. With that feature, the positioning of the collimator can be performed based on the image information of the collimator, which has been captured as an X-ray image in the state where the collimator is set in the snout and the patient is not supported on the patient positioner, and the figure data representing the collimator contour decided in the treatment planning. Thus, the patient can be avoided from being exposed to X-rays when the positioning of the collimator is performed.

According to the present invention, it is possible to reduce a variation in positioning accuracy, to cut unwanted exposure of a patient to radiations, and to increase the efficiency of positioning operations.

Also, according to the present invention, it is possible to reduce the exposure of the patient to X-rays irradiated for the positioning.

DESCRIPTION OF THE PREFERRED EMBODIMENTS

Embodiments of a positioning system and method for radiation therapy according to the present invention will be described below with reference to the drawings.

Figure 1:
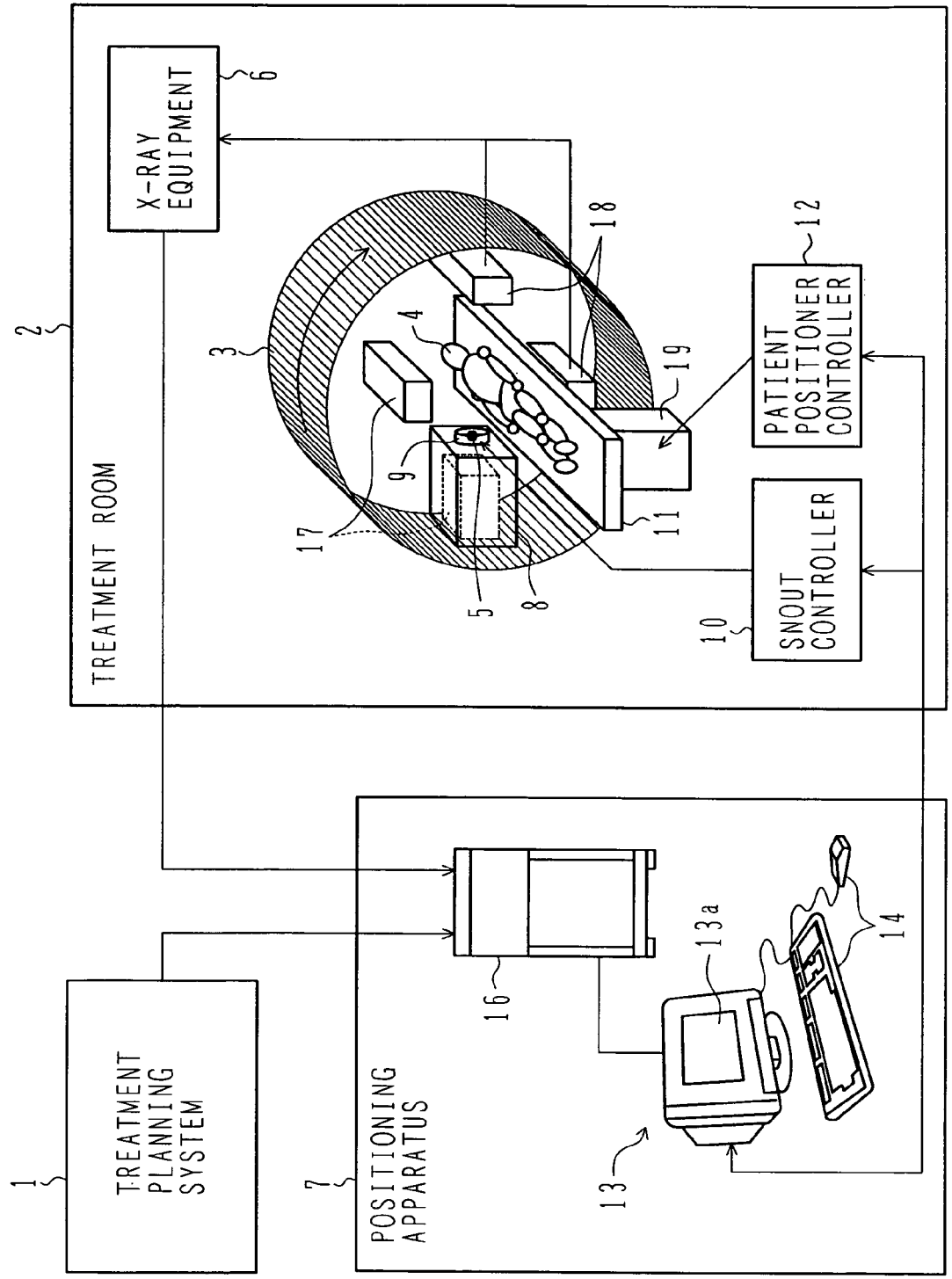
FIG. 1 is an overall schematic view showing an entire construction of a positioning system for particle beam therapy according to one preferred embodiment of the present invention.

FIG. 1 is an overall schematic view showing an entire construction of a positioning system according to one embodiment of the present invention. As shown in FIG. 1, the positioning system of this embodiment is supposed to be used in therapy equipment which employs a particle beam (e.g., a proton beam) and includes a rotating gantry. Note that the present invention is also applicable to other general therapy equipment such as X-ray therapy equipment.

Referring to FIG. 1, the positioning system comprises a treatment planning system 1 for preparing a plan for irradiation of the particle beam per patient (hereinafter referred to as a "treatment plan"), X-ray equipment (image capturing system) 6 disposed within a rotating gantry 3 inside a treatment room 2 and used to view both the position of a patient 4, who is held immobilized on a patient positioner 11 (e.g., a bed or a chair), and the position of a collimator 5, a positioning apparatus 7 for executing various kinds of processing related to positioning of the patient 4 based on treatment planning information from the treatment planning system 1 and image information from the image capturing system 6, a snout 9 rotatably mounted to a fore end of an irradiation nozzle 8 and including the collimator 5 set therein, a snout controller 10 for controlling the rotation of the snout 9, and the patient positioner controller 12 for controlling the operation of the patient positioner 11 (e.g., the bed or the chair) on which is held immobilized the patient 4.

The positioning apparatus 7 comprises a processing unit 13 having a monitor (display) 13a, an input unit 14 including, e.g., a keypad and a mouse, and a medical image server (image information storage) 16 in which are stored images used for the positioning. Further, the X-ray equipment 6 includes two sets of X-ray equipment each comprising an X-ray tube device 17 and an X-ray receiver 18, (the two sets being installed to be able to capture images in the direction of the irradiation beam and a direction crossing the direction of the irradiation beam at an angle of 90°). Those two sets of X-ray equipment are rotatable about the isocenter together with the rotation of the rotating gantry 3.

Figure 2:
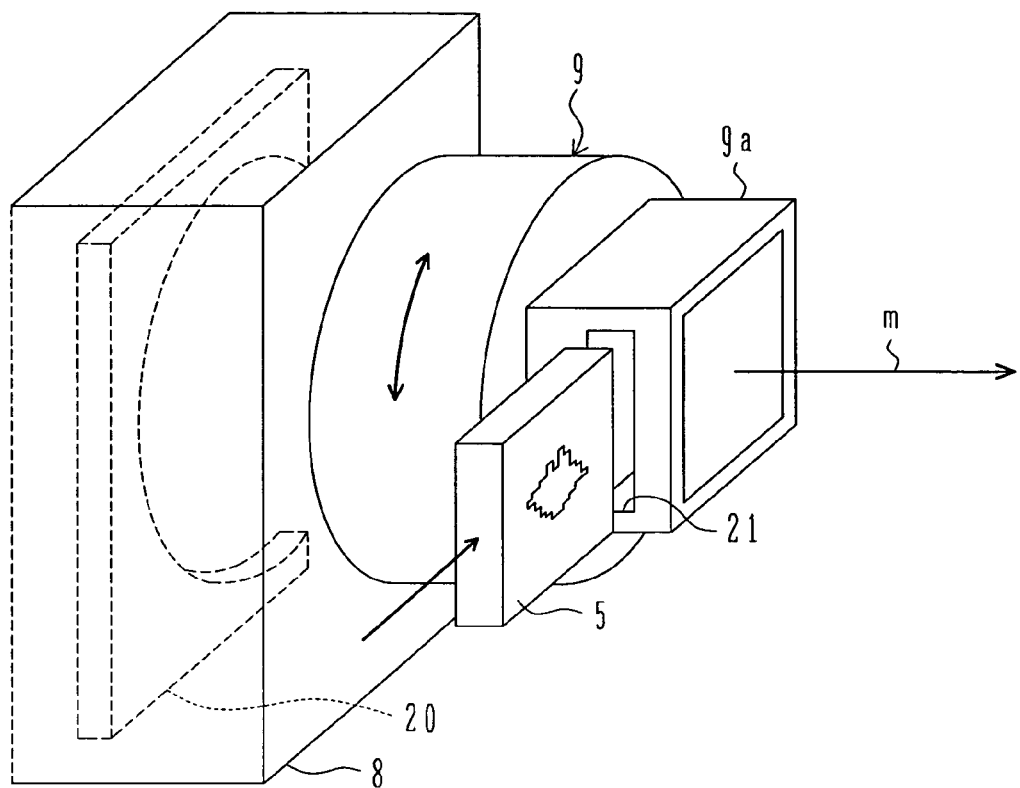
FIG. 2 is a perspective view of a fore end portion of an irradiation nozzle, the view showing an entire structure of a snout.

FIG. 2 is a perspective view of a fore end portion of the irradiation nozzle 8, the view showing an entire structure of the snout 9. The snout 9 is rotatably mounted to the fore end of the irradiation nozzle 8 and is rotated about an irradiation beam axis m by the snout drive unit 20 in accordance with a signal from the snout controller 10. An opening 21 is formed in a lateral surface of a collimator placement portion 9a of the snout 9 such that the collimator 5 can be inserted and withdrawn through the opening 21.

Figure 3:
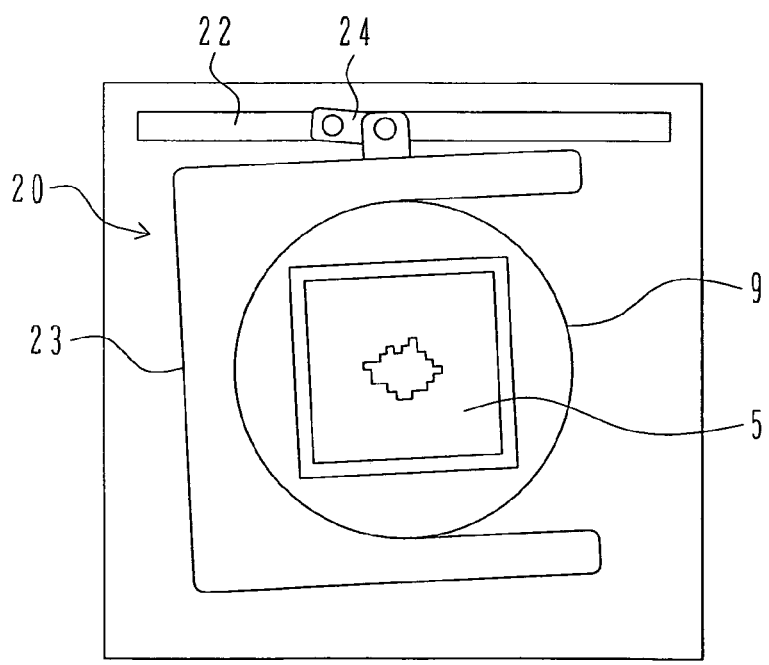
FIG. 3 is a simplified view showing an entire structure of a snout drive unit shown in FIG. 2, looking from the direction of the isocenter (target irradiation center)

FIG. 3 is a simplified view showing an entire structure of the snout drive unit 20, looking from the direction aligned with the isocenter. As shown in FIG. 3, the snout drive unit 20 comprises a parallel driving unit 22, a rotation driving unit 23, and a link mechanism 24 for coupling the parallel driving unit 22 and the rotation driving unit 23 with each other. The parallel driving unit 22 is driven to move in parallel in accordance with a signal from the snout controller 10, whereupon the rotation driving unit 23 is rotated through the link mechanism 24. As a result, the snout 9 coupled to the rotation driving unit 23 is rotated and the collimator 5 set in the collimator placement portion 9a of the snout 9 is also rotated together.

Figure 4:
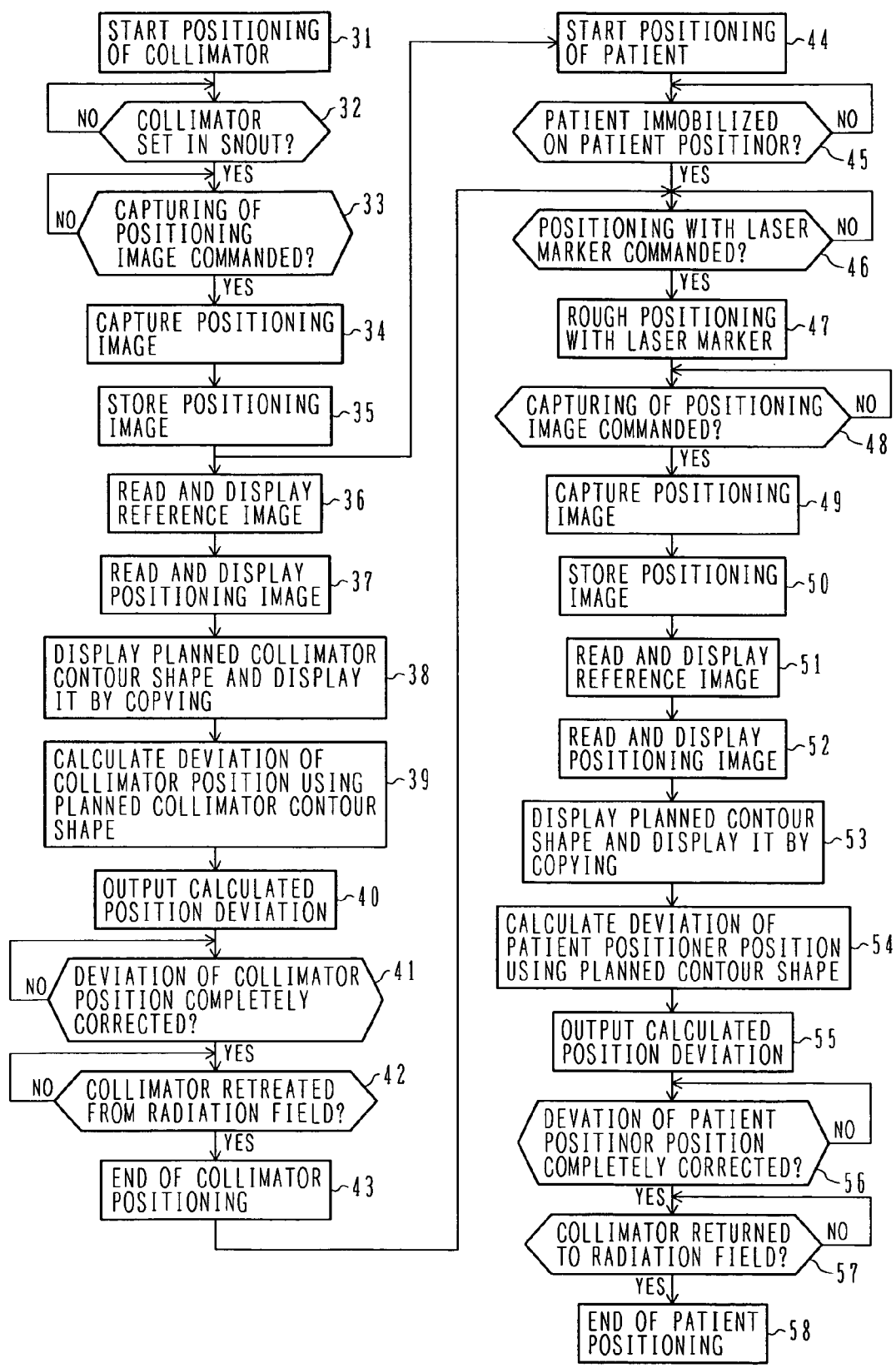
FIG. 4 is a chart of control flow executed by a processing unit of a positioning apparatus shown in FIG. 1.

FIG. 4 is a chart of control flow executed by the processing unit 13 of the positioning apparatus 7. The procedures for positioning the patient 4 and the collimator 5, which are executed by the positioning system of this embodiment, will be described below with reference to FIG. 4. The control flow is started in response to an appropriate positioning start command (e.g., a command input through the input unit 14) from an operator.

As advanced preparations, an image of the patient is first captured by X-ray CT in order to decide the treatment plan. In the treatment planning, the position and size of an affected part in the patient body are confirmed by using the X-ray CT image for decision of the irradiation direction, the dose, etc. Also, during the treatment planning, an X-ray image in a plane passing the origin of a reference coordinate system fixed in the positioning system, i.e., the isocenter (target irradiation center), and being perpendicular to the direction toward an X-ray source is formed as a simulation image, from the CT image in the treatment planning system. That simulation image is called a reference image. In other words, the reference image is a DRR (Digital Reconstructed Radiograph) image that is produced from the CT image obtained during the treatment planning. The reference image is transmitted to the positioning apparatus 7 and is stored in the medical image server 16.

Further, in the present invention, during the treatment planning, information of a planned collimator contour shape is registered in image information of the reference image instead of capturing the collimator contour shape in the actual image, and is also transmitted from the treatment planning system 1 to be stored in the medical image server 16 of the positioning apparatus 7.

The planned collimator contour shape is decided depending on the size and shape of the affected part (tumor) in the patient body and is registered such that the planned collimator contour shape is positioned over the affected part in the patient body appearing in the reference image (namely, the affected part in the patient body is displayed while being included in the planned collimator contour shape). In addition, the planned collimator contour shape is displayed at a center of the reference image (i.e., a center of a reference image display area), and the affected part (tumor) in the patient body is registered to be displayed at the center of the reference image (i.e., the center of the reference image display area).

After the end of the above-described preparations, the procedures of the control flow shown in FIG. 4 are started.

First, the positioning of the collimator 5 is started (step 31). It is determined whether the collimator 5 is set (step 32). More specifically, determination is made as to whether setting of the collimator 5 into the collimator placement portion 9a of the snout 9 by the operator is detected, for example, by an appropriate detection sensor (not shown). If the setting of the collimator 5 is detected, it is then determined whether a command for capturing an X-ray image is inputted from the operator (step 33). If the operator inputs a command to start the capturing of the X-ray image from the input unit 14 of the positioning apparatus 7, an aperture image containing the contour of the collimator 5 is captured as a positioning image by the X-ray equipment 6 (step 34). After the end of the image capturing, the captured positioning image is read from the X-ray equipment 6 to be stored in the medical image server 16 of the positioning apparatus 7 (step 35).

Then, the reference image is read from the medical image server 16 and is displayed on the monitor 13a (step 36). Also, the positioning image stored in above step 35 is read from the medical image server 16 and is displayed on the monitor 13a (step 37).

Figure 5:
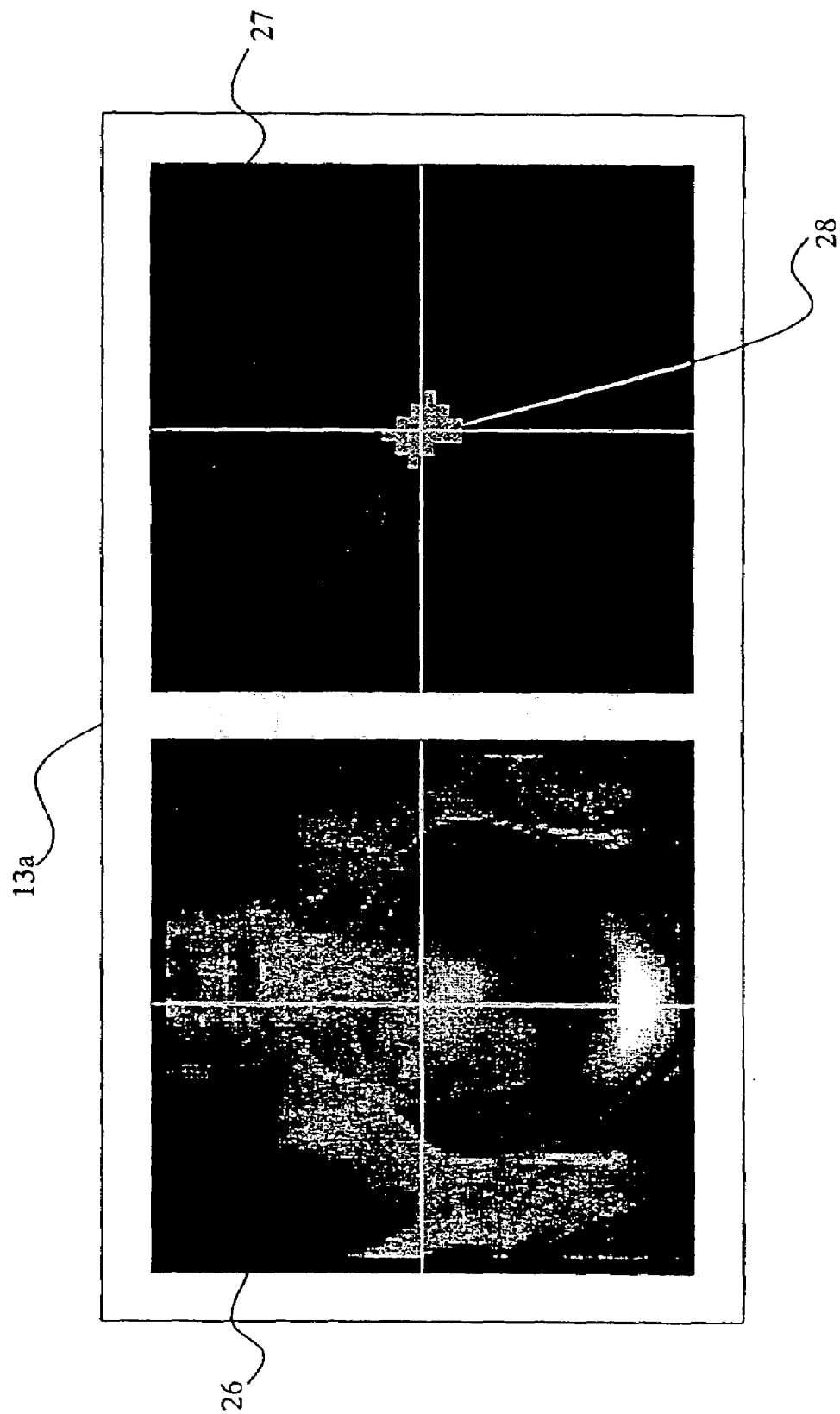
FIG. 5 shows one example of a monitor screen when a reference image and a positioning image are displayed in collimator positioning.

FIG. 5 shows one example of a screen displayed on the monitor 13a at that time. As shown in FIG. 5, a reference image 26 and a positioning image 27 are displayed side by side on the monitor 13a. As described above, the affected part (tumor) in the patient body is displayed at the center of the reference image (i.e., the center of the reference image display area). Also, in the display area of the reference image 26, perpendicularly crossed guide lines extending in the vertical direction and the horizontal direction while passing the center of the reference image 26 are displayed as a position guide for the operator. On the positioning image 27, an actual collimator contour shape 28 captured in above step 34 is superimposed. The center position of the collimator contour shape 28 is matched with the isocenter (i.e., the origin of the reference coordinate system fixed in the positioning system), and the collimator contour shape 28 is displayed at the center of the positioning image 27 (i.e., the center of the positioning image display area). The center of the positioning image 27 (i.e., the center of the positioning image display area) is matched with the isocenter. Also, in the display area of the positioning image 27, perpendicularly crossed guide lines extending in the vertical direction and the horizontal direction while passing the center of the positioning image 27 are displayed as a position guide for the operator.

While this embodiment is illustrated as displaying the reference image 26 and the positioning image 27 on one monitor 13*a*, the monitor 13*a* may be used to display one of those images and another monitor may be additionally used to display the other image.

In the state where the reference image 26 and the positioning image 27 are displayed on the monitor 13*a*, figure data representing the planned collimator contour shape decided in the treatment planning, e.g., line drawing data (contour shape) 29, is displayed on the reference image 26, and the line drawing data 29 is also displayed by copying at the same coordinate position on the positioning image 27, i.e., at the center of the display area of the positioning image 27 (isocenter position) (step 38). The line drawing data 29 representing the planned collimator contour shape is, as described above, previously registered in the image information of the reference image 26 during the treatment planning. In other words, the reference image 26 is stored in the medical image server 16 as the image information containing the line drawing data. Alternatively, the line drawing data 29 may be stored in the medical image server 16 just as line drawing information separately from the reference image 26. In such a case, data of both the images 26, 27 and the line drawing data 29 are read and displayed in a superimposed manner when those data are displayed on the monitor 13*a*.

Figure 6:
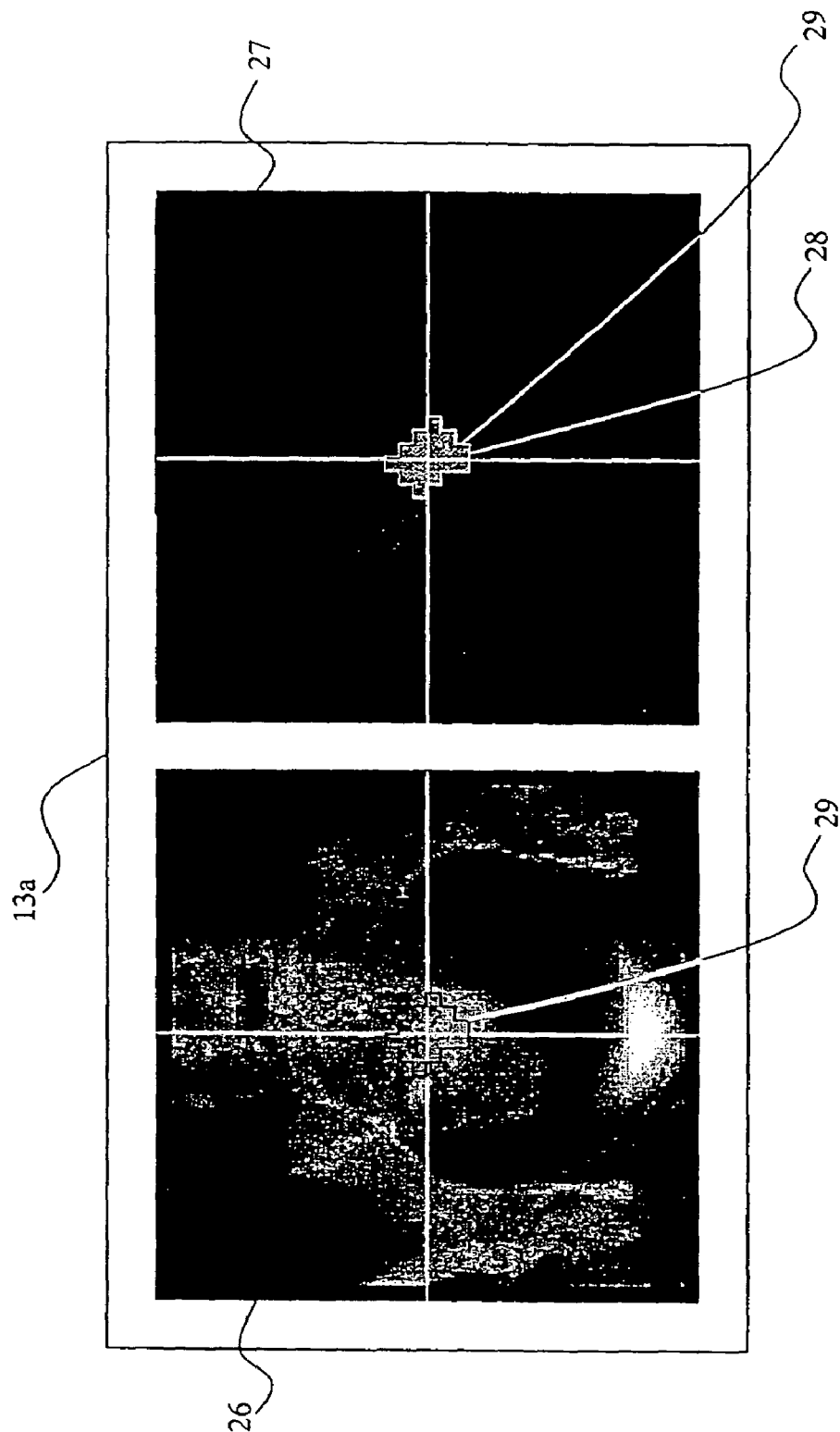
FIG. 6 shows one example of a monitor screen when line drawing data (contour shape) is displayed on each of the reference image and the positioning image in the collimator positioning.

FIG. 6 shows one example of a screen displayed on the monitor 13*a* when the line drawing data 29 is displayed on each of the reference image 26 and the positioning image 27. As shown in FIG. 6, the line drawing data 29 representing the planned collimator contour shape is displayed on the reference image 26 such that its center is matched with the intersect point of the perpendicularly crossed guide lines, and the line drawing data 29 is also displayed on the positioning image 27 such that its center is matched with the intersect point of the perpendicularly crossed guide lines. Stated another way, the line drawing data 29 on the positioning image 27, which represents the planned collimator contour shape, is displayed by copying at the same coordinate position as that of the line drawing data 29 on the reference image 26. Also, the actual collimator contour shape 28 on the positioning image 27 is displayed with a slight deviation from the line drawing data 29 representing the planned collimator contour shape. In the illustrated example, it is seen that the position of the collimator 5 is slightly deviated relative to the planned position.

Then, the position deviation of the collimator 5 is calculated (step 39) based on the line drawing data 29 which has been displayed by copying on the positioning image 27 in above step 37. In this embodiment, the position deviation of the collimator 5 is calculated by using one of two methods described below.

Figure 7:
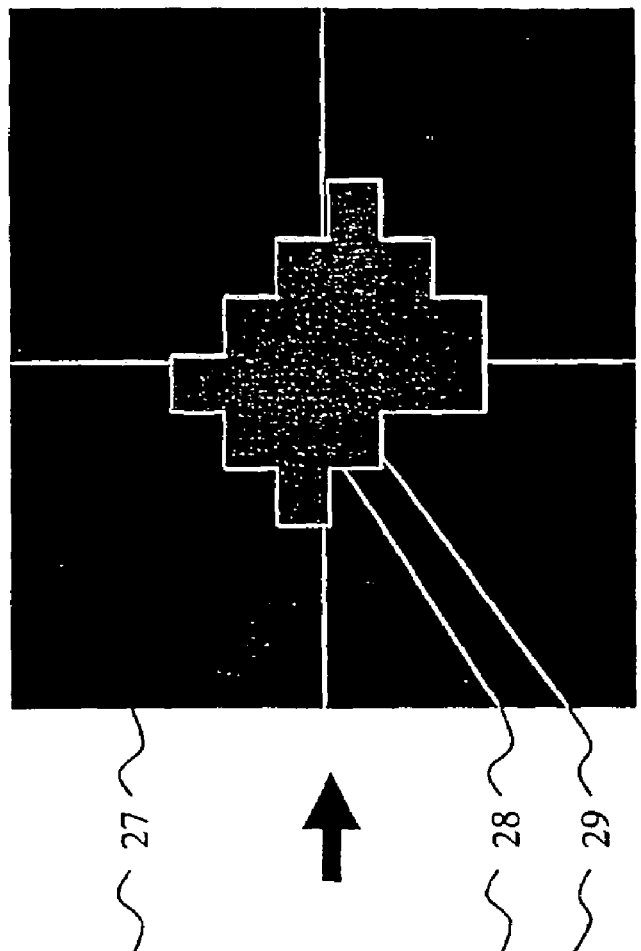
FIGS. 7A and 7B each show, in enlarged scale, a central area (i.e., an area near the isocenter) of the positioning image on which is displayed the line drawing data in a superimposed manner, for explaining a first method of calculating a position deviation in the collimator positioning.
Figure 7:
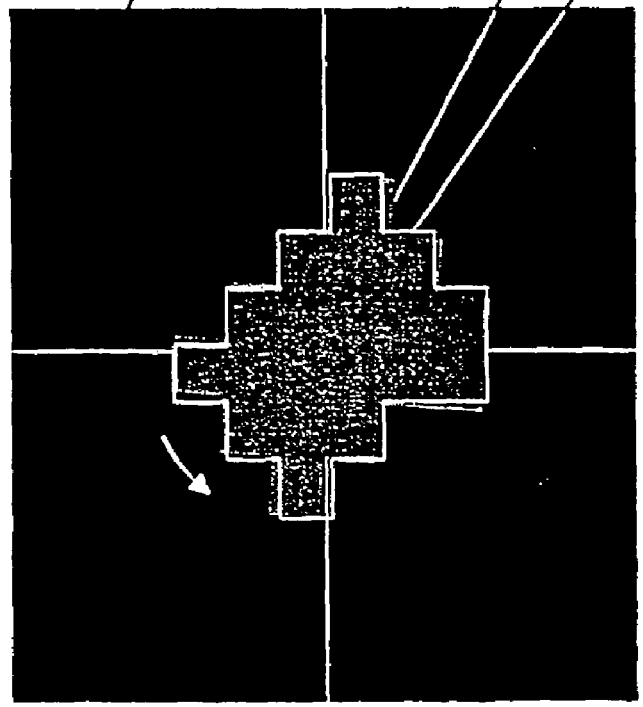

A first method will be described below with reference to FIGS. 7A and 7B. FIGS. 7A and 7B each show, in enlarged scale, a central area (i.e., an area near the isocenter) of the positioning image 27 displayed on the monitor 13*a*, including the line drawing data 29 also displayed in a superimposed relation. In FIGS. 7A and 7B, the operator can move (rotate in this case) the positioning image 27 by operating the input unit 14. More specifically, in the state where the line drawing data 29 displayed on the positioning image 27 is deviated from the actual collimator contour shape 28 superimposed on the positioning image 27 (i.e., in the state shown in FIG. 7A), the operator rotates the positioning image 27 by using the input unit 14 so that the line drawing data 29 is exactly matched with the actual collimator contour shape 28 (the resulting state is shown in FIG. 7B). The processing unit 13 calculates the position deviation of the collimator 5 (i.e., the amount of rotation of the snout 9) based on the amount by which the positioning image 27 has been rotated at that time.

Figure 8:
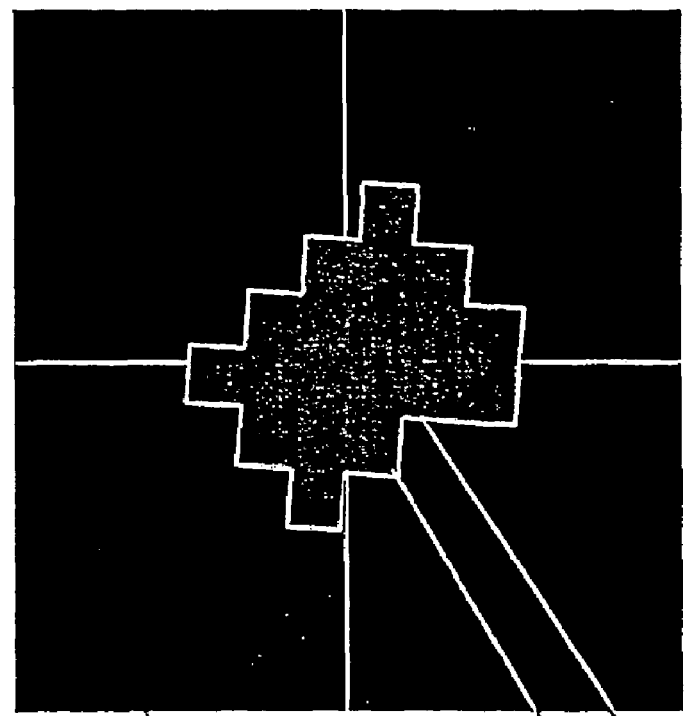
FIGS. 8A and 8B each show, in enlarged scale, the central area (i.e., the area near the isocenter) of the positioning image on which is displayed the line drawing data in a superimposed manner, for explaining a second method of calculating a position deviation in the collimator positioning.
Figure 8:
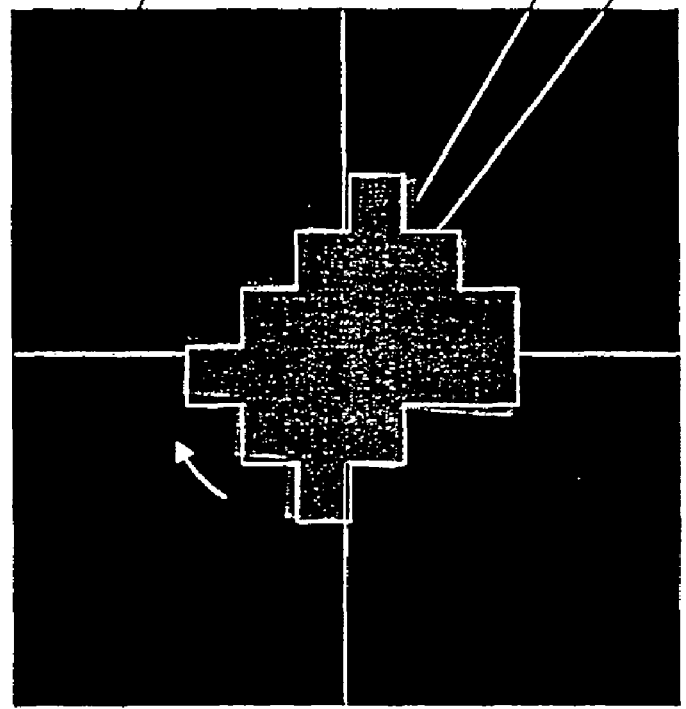

A second method will be described below with reference to FIGS. 8A and 8B. In FIGS. 8A and 8B, the operator can move (rotate in this case) the line drawing data 29 representing the planned collimator contour shape by operating the input unit 14. More specifically, in the state where the line drawing data 29 displayed on the positioning image 27 is deviated from the actual collimator contour shape 28 superimposed on the positioning image 27 (i.e., in the state shown in FIG. 8A), the operator rotates the line drawing data 29 by using the input unit 14 so that the line drawing data 29 is exactly matched with the actual collimator contour shape 28 (the resulting state is shown in FIG. 8B). The processing unit 13 calculates the position deviation of the collimator 5 (i.e., the amount of rotation of the snout 9) based on the amount by which the line drawing data 29 has been rotated at that time.

The position deviation of the collimator 5 calculated by one of the above-described two methods is outputted, as collimator positioning information, to the snout controller 10 (step 40). Then, it is determined whether the position deviation of the collimator 5 is completely corrected (step 41). More specifically, the snout controller 10 having received the position deviation outputted in above step 40 controls the snout drive unit 20 in accordance with the received position deviation, thereby rotating the snout 9 so as to correct the position deviation of the collimator 5. If the correction of the position deviation is completed, the snout controller 10 transmits a collimator-positioning end signal to the processing unit 13 of the positioning apparatus 7. Thus, it is determined whether the collimator-positioning end signal is inputted from the snout controller 10.

If the position deviation of the collimator 5 is completely corrected, it is determined whether the collimator 5 has been removed (step 42). This determination is made for the necessity of temporarily retreating the collimator 5 from the radiation field such that, when an X-ray image is captured in later-described positioning of the patient 4, an image of the collimator 5 is not taken in the X-ray image. If it is detected that the collimator 5 has been removed from the collimator placement portion 9*a* of the snout 9 by the operator, the collimator positioning is brought to an end (step 43). While this embodiment is described as removing the collimator 5 by the operator, it is also possible, for example, to employ a structure that the collimator placement portion 9*a* of the snout 9 can be turned to such an extent as retreating the collimator 5 from the radiation field with the collimator 5 kept in the set position, for the purpose of increasing workability and reproducibility of the collimator position when the collimator 5 is returned to the set position.

The positioning of the patient 4 is started (step 44) after capturing the positioning image by the X-ray equipment and storing the captured image in steps 34 and 35 with the above-described positioning operation of the collimator 5. First, it is determined whether immobilization of the patient 4 on the patient positioner 11 is completed (step 45). More specifically, determination is made as to whether a signal indicating that the patient 4 has been made immobilized on the patient positioner 11 by, e.g., the operator with the aid of the immobilization device and the immobilizing procedure has been completed is inputted from the operator by using, e.g., the input unit 14. The procedure of immobilizing the patient 4 by, e.g., the operator is performed in parallel to the above-described positioning operation of the collimator 5 in the steps subsequent to step 35.

If the immobilization of the patient 4 on the patient positioner 11 is completed and the positioning operation of the collimator 5 up to step 43 is brought to an end, it is determined whether the start of positioning of the patient 4 with a laser marker is commanded from the operator (step 46). The positioning with the laser marker is rough positioning that is performed by irradiating a laser to the patient 4 during the treatment planning from a laser generator (not shown) mounted to, e.g., a wall of the treatment room 2 to mark the irradiated position, and when the treatment is started, by fixing the laser generator to the same irradiation point as that in the marking step and moving the patient 4 (i.e., the patient positioner 11) so that the marked position on the patient 4 is matched with the laser while the patient body is held immobilized by using the immobilization device. If the command is inputted from the operator, the positioning with the laser marker is performed (step 47).

Then, it is determined whether a command for capturing an X-ray image is inputted from the operator (step 48). If the operator inputs the command to start the capturing of the X-ray image from the input unit 14, the positioning image of the patient 4 immobilized on the patient positioner 11 is captured by the X-ray equipment 6 (step 49), and the positioning image (second image information) is stored in the medical image server 16 (step 50). The positioning image of the patient 4 is image information containing the affected part in the patient body, and it also includes image information of the isocenter position.

Then, the reference image (first image information) is read from the medical image server 16 and is displayed on the monitor 13a (step 51). Also, the positioning image stored in above step 50 is read from the medical image server 16 and is displayed on the monitor 13a (step 52).

In the state where the reference image and the positioning image are displayed on the monitor 13a, as in the above-described collimator positioning, the line drawing data (contour shape) representing the planned collimator contour shape is displayed on the reference image, and it is also displayed by copying at the same coordinate position on the positioning image, i.e., at the center of the display area of the positioning image (isocenter position) (step 53).

Figure 9:
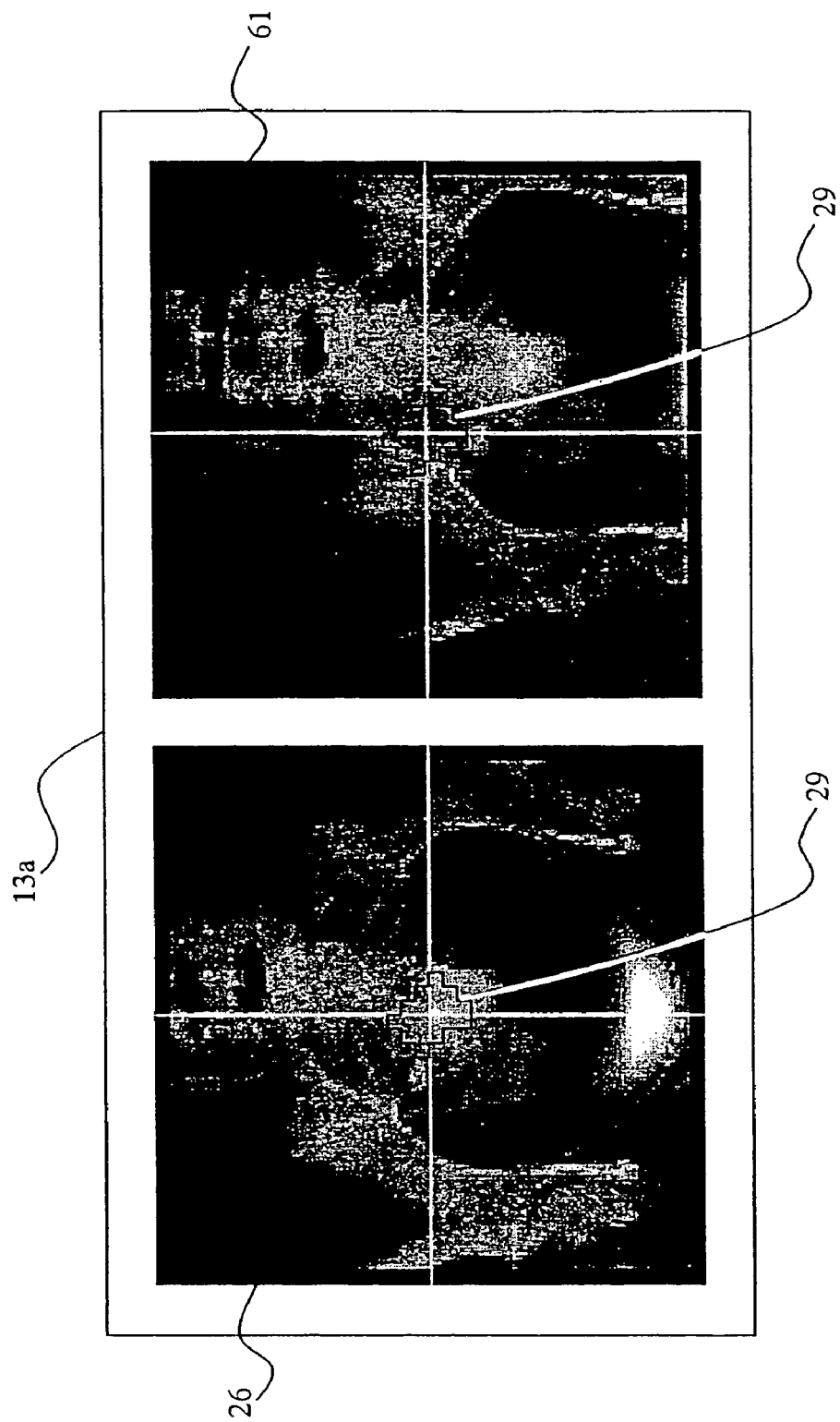
FIG. 9 shows one example of a monitor screen when the line drawing data is displayed on each of the reference image and the positioning image in patient positioning.

FIG. 9 shows one example of a screen displayed on the monitor 13a at that time. In FIG. 9, numeral 26 denotes the reference image and 61 denotes the positioning image. Those two images are displayed side by side. The center of a display area of the positioning image 61 is matched with the isocenter. On the reference image 26, the line drawing data 29 representing the planned collimator contour shape is displayed, and on the positioning image 61, the line drawing data 29 representing the planned collimator contour shape is also displayed by copying. In each of the respective display areas of the reference image 26 and the positioning image 61, perpendicularly crossed guide lines extending in the vertical direction and the horizontal direction while passing the center of each of the reference image 26 and the positioning image 61 are displayed as a position guide for the operator. The line drawing data 29 representing the planned collimator contour shape is displayed on each of the reference image 26 and the positioning image 27 such that its center is matched with the intersect point of the perpendicularly crossed guide lines. Stated another way, the line drawing data 29 on the positioning image 61, which represents the planned collimator contour shape, is displayed by copying at the same coordinate position (i.e., the isocenter position) as that of the line drawing data 29 on the reference image 26. While this embodiment is illustrated as displaying the reference image 26 and the positioning image 61 on one monitor 13a, the monitor 13a may be used to display one of those images and another monitor may be used to display the other image. Further, as described above, the line drawing data 29 representing the planned collimator contour shape is previously registered in the image information of the reference image 26 during the treatment planning.

Because the collimator positioning is completed at this time, it can be said that the line drawing data 29 displayed by copying on the positioning image 61 in FIG. 9 is identical to the actual contour shape of the collimator 5. In FIG. 9, therefore, the two images are displayed such that the position of the line drawing data (first figure data) 29 relative to the image information (e.g., the positions of the tumor and the skeleton) of the reference image 26 is slightly deviated from the position of the line drawing data (second figure data) 29 relative to the image information (e.g., the positions of the tumor and the skeleton) of the positioning image 61. In the illustrated example, it is seen that the position of the patient 4 is slightly deviated relative to the planned position.

Then, the position deviation of the patient 4 (i.e., the patient positioner 11) is calculated (step 54) using the line drawing data (contour shape) 29 which has been displayed by copying on the positioning image 61 in above step 53. In this embodiment, the position deviation of the patient 4 is calculated by using one of two methods described below.

Figure 10:
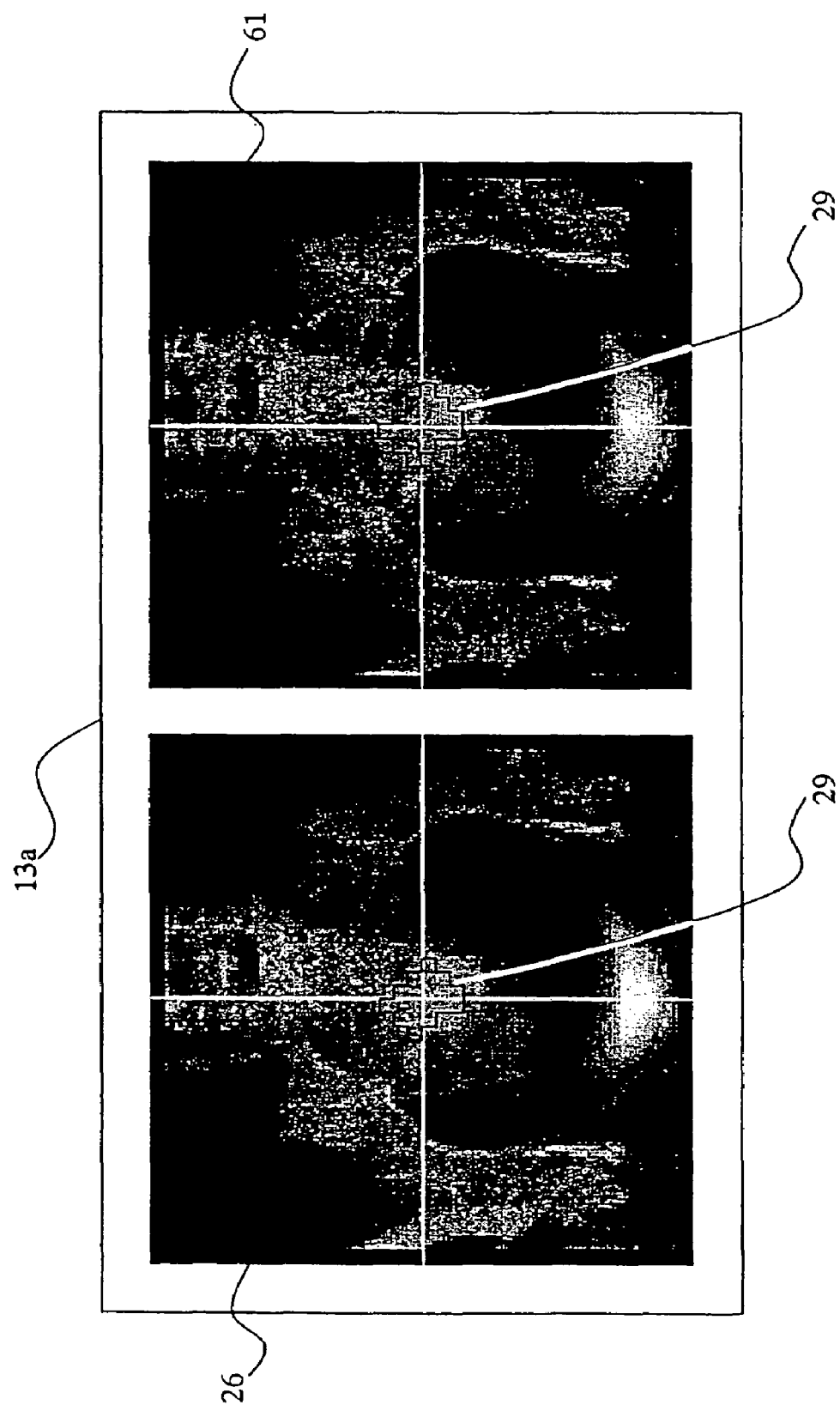
FIG. 10 shows the reference image and the positioning image on which is displayed the line drawing data in a superimposed manner, for explaining a method of calculating a first position deviation in the patient positioning.

A first method will be described below with reference to FIG. 10. In FIG. 10, the operator can move and rotate the positioning image 61 by operating the input unit 14. More specifically, in the state where the position of the line drawing data 29 relative to the image information of the reference image 26 is slightly deviated from the position of the line drawing data (second figure data) 29 relative to the image information of the positioning image 61 (i.e., in the state shown in FIG. 9), the operator moves the positioning image 61 to a desired position by using the input unit 14 so that the relative positional relationship between the line drawing data 29 on the positioning image 61 and the image information of the positioning image 61 is identical to the relative positional relationship between the line drawing data 29 on the reference image 26 and the image information of the reference image 26, namely so that the tumor position on the positioning image 61 falls within the line drawing data 29 on the positioning image 61, while referring to the relationship between the reference image 26 and the line drawing data 29, particularly, the tumor position in the line drawing data 29 (the resulting state is shown in FIG. 10). The processing unit 13 calculates the position deviation of the patient 4 (i.e., the patient positioner 11) based on the amounts by which the positioning image 61 has been moved and rotated at that time.

Figure 11:
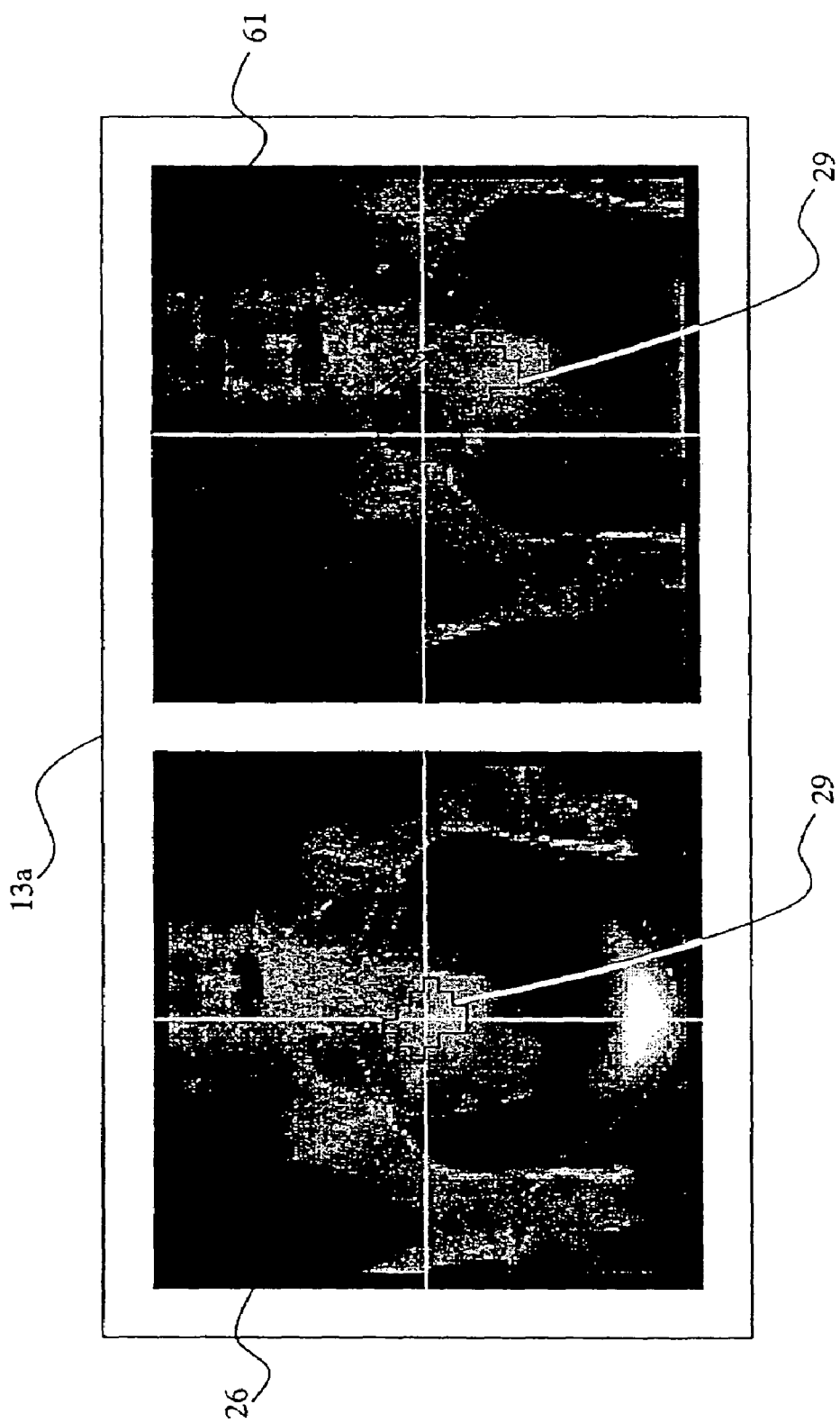
FIG. 11 shows the reference image and the positioning image on which is displayed the line drawing data in a superimposed manner, for explaining a method of calculating a second position deviation in the patient positioning.

A second method will be described below with reference to FIG. 11. In FIG. 11, the operator can move and rotate the line drawing data 29 on the positioning image 61 by operating the input unit 14. More specifically, as with the above first method, in the deviated state of FIG. 9, the operator moves the line drawing data 29 to a desired position by using the input unit 14 so that the relative positional relationship between the line drawing data 29 on the positioning image 61 and the image information of the positioning image 61 is identical to the relative positional relationship between the line drawing data 29 on the reference image 26 and the image information of the reference image 26, namely so that the tumor position on the positioning image 61 falls within the line drawing data 29 on the positioning image 61, while referring to the relationship between the reference image 26 and the line drawing data 29, particularly, the tumor position in the line drawing data 29 (the resulting state is shown in FIG. 11). The processing unit 13 calculates the position deviation of the patient 4 (i.e., the patient positioner 11) based on the amounts by which the line drawing data 29 has been moved and rotated at that time.

In any of those two methods, if necessary, an aperture image (see FIGS. 5 and 6 described above) may be formed by trimming the positioning image 61 in accordance with the line drawing data 29.

Though not specifically described above, positioning operation using a positioning image captured by the X-ray equipment 6 in the direction forming an angle of 90° relative to the direction of the irradiation beam cannot be performed using the line drawing data 29 representing the planned collimator contour shape. In that positioning operation, therefore, the position deviation is calculated in a similar manner to that described above by using other line drawing data representing, e.g., the organ shape, the bone shape, the body contour shape, or the clinical (or planning) target volume shape.

The position deviation of the patient 4 calculated by one of the above-described two methods is outputted, as patient-positioner positioning information, to the patient positioner controller 12 (step 55). Then, it is determined whether the position deviation of the patient 4 is completely corrected (step 56). More specifically, the patient positioner controller 12 having received the position deviation outputted in above step 55 controls the patient positioner drive unit 19 in accordance with the received position deviation, thereby moving and rotating the patient positioner 11 so as to correct the position deviation of the patient 4. If the correction of the position deviation is completed, it is determined whether the collimator 5 is returned to the radiation field (step 57). If it is detected that the collimator 5 is inserted to the collimator placement portion 9a of the snout 9 and returned to the set position again by the operator, the positioning of the patient 4 is brought to an end (step 58).

In the foregoing, the processing unit 13 of the positioning apparatus 7 functions as a processing control unit for producing positioning information of the patient positioner in claim 1, and as a processing control unit for producing positioning information of the collimator (first position information) and positioning information of the patient positioner (second position information) in claim 9. Also, the processing unit 13 of the positioning apparatus 7 functions as a collimator positioning apparatus in claim 10, and as a patient positioning apparatus in claim 16.

The above-described positioning system of this embodiment provides the following advantages.

(1) Improvement of Positioning Accuracy with Use of Line Drawing Data

With the above-mentioned related art disclosed in Patent Document 2 in which the operator inputs the calculation points at corresponding positions in the reference image and the comparative image on the screen for calculating the position deviation, when a sufficient contrast is not obtained in, e.g., the positioning image, or when the immobilization device for holding the patient in the immobilized state or other component is additionally taken in the image, the calculation points cannot be precisely set. Further, the above-mentioned related art disclosed in Patent Document 3 cannot also be applied to such a case because it employs the method of calculating the position deviation based on the comparison of pixel values.

In contrast, with this embodiment, in the positioning of the collimator 5, the position deviation is calculated by, as shown in FIGS. 5 and 6, displaying the line drawing data 29 on the reference image 26, which represents the planned collimator contour shape, by copying at the same coordinate position (i.e., the isocenter position) on the positioning image 27 on which the contour of the collimator 5 is superimposed. Therefore, the collimator positioning can be performed without suffering from influences due to an insufficient contrast of the positioning image and accidental capturing of an image of the extra component at all. Also, in the positioning of the patient 4, as described above, the position deviation is calculated by displaying the line drawing data 29 at the same coordinate position (i.e., the isocenter position) on each of the reference image 26 and the positioning image 61, and by moving the positioning image 61 (or the line drawing data 29) to a desired position by using the input unit 14 so that the tumor position on the positioning image 61 falls within the line drawing data 29 on the positioning image 61, while referring to the positional relationship between the line drawing data 29 and the tumor position in the positioning image 61. Therefore, the influences due to an insufficient contrast of the positioning image and accidental capturing of an image of the extra component can be reduced. Thus, this embodiment is able to improve the positioning accuracy. As a result, unwanted exposure of the patient to radiations can also be reduced.

(2) Reduction of Exposure to X-Rays

In the positioning system of this embodiment, as described above, the positioning of the collimator 5 is performed through the steps of displaying the line drawing data 29 representing the planned collimator contour shape on the positioning image 27, moving the positioning image 27 or the line drawing data 29 on the screen image of the monitor 13a so that the contour shape 28 of the collimator 5 captured in the positioning image 27 is matched with the line drawing data 29, calculating the position deviation of the collimator 5 based on the amount by which the positioning image 27 or the line drawing data 29 has been moved, and rotating the snout 9 in accordance with the calculated position deviation. With such a positioning method, the positioning of the collimator 5 can be performed by using the positioning image 27 obtained by capturing an X-ray image of only the collimator 5 without including the patient 4 (namely, the positioning image 27 obtained by capturing an X-ray image of only the collimator 5 in the state where the patient 4 is not held on the patient positioner 11). As a result, after capturing the X-ray image of the collimator 5 for the positioning of the collimator 5, it is possible to start the operations of making the patient 4 immobilized on the patient positioner 11, and performing the positioning of the patient 4 capturing an X-ray image of the patient 4. This avoids the patient 4 from being exposed to X-rays twice, i.e., when the positioning of the collimator 5 and the positioning of the patient 4 are performed by capturing the X-ray images thereof. Thus, the exposure of the patient to X-rays during the positioning operations can be reduced.

(3) Reduction of Positioning Time, etc. Due to Collimator Automatic Positioning

In this embodiment, the positioning image 27 or the line drawing data 29 is moved so that the line drawing data 29 representing the planned collimator contour shape and the contour shape 28 of the collimator 5 captured in the positioning image 27 are matched with each other. The position deviation of the collimator 5 is calculated based on the amount by which the positioning image 27 or the line drawing data 29 has been moved, and the positioning of the collimator 5 is automatically performed in accordance with the calculated position deviation. Thus, since the positioning of the collimator 5 can be automatically performed, it is possible to reduce the time required for the positioning of the collimator 5 and to cut labor of the operator in comparison with the related art in which the collimator position is corrected by manually rotating the snout by the operator, or by inputting the amount of rotation of the snout based on judgment of the operator and rotating the snout by a drive unit. Further, the related art has the problem that, when the operator is changed in turn, the inputted position deviation may vary, thus resulting in reduction of the accuracy and reproducibility of the positioning. In contrast, with this embodiment, since the position deviation is automatically calculated for the positioning just by simple operation of making respective contours on two images matched with each other, the accuracy and reproducibility of the positioning can be improved.

(4) Reduction of Positioning Time with Parallel Progress of Operations

In this embodiment, as described above with reference to FIG. 4, the positioning of the patient 4 is started from the point in time at which the X-ray image capturing for the positioning of the collimator 5 is completed. Therefore, the operator or other person can perform the operation of making the patient 4 immobilized on the patient positioner 11 in parallel while the operation of positioning the collimator 5 is performed after capturing the X-ray image of the collimator 5. Accordingly, in comparison with the related art in which the collimator positioning is performed after the positioning of the patient without performing the two positioning operations in parallel, the time required for the positioning operations (i.e., the collimator positioning and the patient positioning) can be reduced as a result of the parallel operations.

Figure 12:
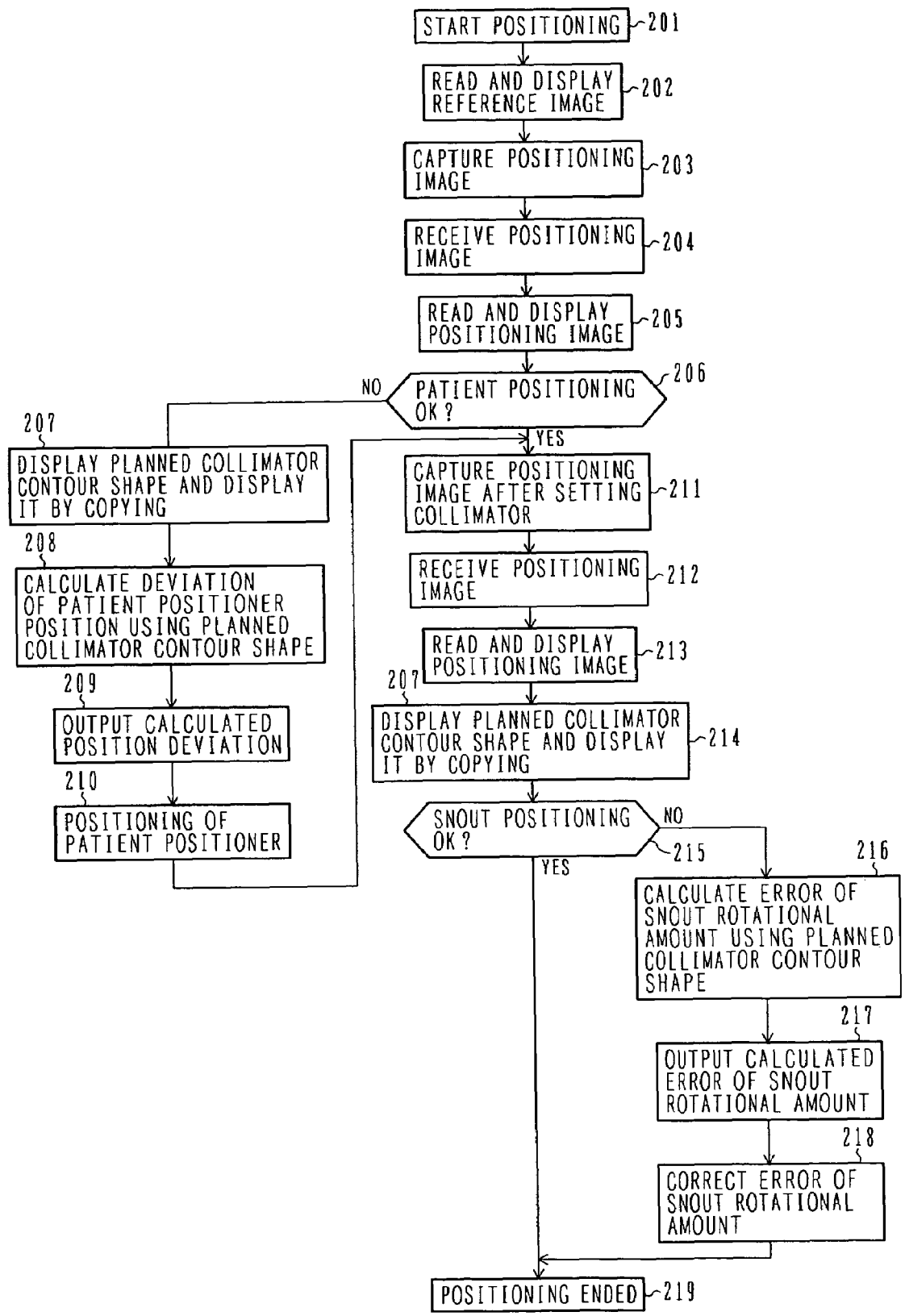
FIG. 12 is a chart of control flow for explaining a positioning method according to another embodiment of the present invention.

Another embodiment of the present invention will be described below with reference to FIG. 12. The other embodiment differs from the above embodiment in procedures of the positioning method. FIG. 12 is a chart of control flow showing the procedures of the positioning method according to the other embodiment. An entire construction of a positioning system used for implementing the positioning method according to the other embodiment is the same as that in the above embodiment. The following description is made with reference to FIGS. 1-3 and 5-11 on an assumption that the same components and matters in the system construction and screens displayed on the monitor according to the positioning method are denoted the same numerals in those drawings. The control flow shown in FIG. 12 is executed by the processing unit 13 of the positioning apparatus 7.

Prior to starting the positioning method of this embodiment, as in the above embodiment, during the treatment planning, information of a planned collimator contour shape is registered in image information of the reference image instead of capturing the collimator contour shape in the actual image, and is also transmitted from the treatment planning system 1 to be stored in the medical image server 16 of the positioning apparatus 7.

After rough positioning with the aid of a laser maker, the positioning operation is started (step 201). First, the operator commands the positioning apparatus 7 to read the stored reference image from the medical image server 16 and to display the reference image on the monitor 13a (step 202). Then, a positioning image of the patient 4 held immobilized on the patient positioner 11 is captured by the X-ray equipment 6 (step 203), and the positioning image is transmitted from the X-ray equipment 6 to be stored in the medical image server 16 (step 204). Further, the operator commands the positioning apparatus 7 to read the stored positioning image from the medical image server 16 and to display the positioning image on the monitor 13a (step 205).

When the reference image and the positioning image are displayed, the operator compares both the images, for example, by superimposing those two images one on the other, and judges the accuracy in positioning of the patient (step 206). If the judgment result requires a position deviation between the two images to be calculated, the planned collimator contour shape (line drawing data 29) registered in the image information of the reference image is displayed on the reference image, and it is also displayed by copying at the same coordinate position on the positioning image (i.e., the isocenter position at the center of the display area of the positioning image) (step 207).

A screen displayed on the monitor 13a at that time is the same as that shown, by way of example, in FIG. 9 related to the above embodiment. In FIG. 9, numeral 26 denotes the reference image and 61 denotes the positioning image. Those two images are displayed side by side. On the reference image 26, the line drawing data 29 representing the planned collimator contour shape is displayed, and on the positioning image 61, the line drawing data 29 representing the planned collimator contour shape is also displayed by copying at the same coordinate position (i.e., isocenter position at the center of the display area of the positioning image 61).

The position deviation of the patient 4 held immobilized on the patient positioner 11 is calculated (step 208) based on the line drawing data 29 representing the planned collimator contour shape which has been displayed by copying on the positioning image 61 as described above. The position deviation can be calculated in a similar manner to that in the above embodiment. Stated another way, there are two methods for calculating the position deviation. According to a first method, as described above with reference to FIG. 10, the position deviation is calculated by using, as a reference region for the positioning, the line drawing data 29 which represents the planned collimator contour shape and is displayed by copying, and moving the positioning image 61 to be set at a desired position relative to the line drawing data 29. According to a second method, as described above with reference to FIG. 11, the position deviation is calculated by moving the line drawing data 29, which represents the planned collimator contour shape and is displayed by copying, on the positioning image 61 to a desired position.

The position deviation calculated by one of the above-described two methods is outputted from the positioning apparatus 7 to the patient positioner controller 12 (step 209). The operator commands the patient positioner controller 12 to move and rotate the patient positioner 11 in three dimensional directions in accordance with the outputted position deviation (step 210).

After the completion of the patient positioning, the operator sets the collimator 5 in the snout 9 and captures a positioning image of the patient 4 held immobilized on the patient positioner 11 by using the X-ray equipment 6 (step 211). The positioning image is transmitted from the X-ray equipment 6 to be stored in the medical image server 16 (step 212). Further, the operator commands the positioning apparatus 7 to read the stored positioning image from the medical image server 16 and to display the positioning image on the monitor 13a (step 213).

A screen displayed on the monitor 13a at that time is the same as that shown, by way of example, in FIG. 5 related to the above embodiment. In FIG. 5, numeral 27 denotes the positioning image and 28 denotes the actual collimator contour shape. In the illustrated example, the reference image 26 and the positioning image 27 displayed side by side.

Then, the operator commands to display the line drawing data 29 representing the planned collimator contour shape, which is registered in the image information of the reference image, not only on the reference image, but also on the positioning image by copying at the same coordinate position (i.e., isocenter position at the center of the display area of the positioning image) (step 214).

A screen displayed on the monitor 13a at that time is the same as that shown, by way of example, in FIG. 6 related to the above embodiment. More specifically, on the reference image 26, the line drawing data 29 representing the planned collimator contour shape is displayed, and on the positioning image 27, the line drawing data 29 representing the planned collimator contour shape is also displayed by copying at the same coordinate position (i.e., isocenter position at the center of the display area of the positioning image 61). As shown in FIG. 6, therefore, the actual collimator contour shape 28 and the line drawing data 29 representing the planned collimator contour shape are displayed on the positioning image 27 in relation slightly deviated from each other. In the illustrated example, it is seen that the position of the collimator 5 is slightly deviated relative to the planned position.

By comparing the line drawing data 29 representing the planned collimator contour shape, which is displayed by copying on the positioning image 27, with the actual collimator contour shape 28 which is superimposed on the positioning image 27, the operator judges the accuracy in positioning of the snout 9 in which is set the collimator 5 (step 215). If the judgment result requires calculation of an error in the amount of snout rotation, the error in the amount of rotation of the snout 9 is calculated based on the planned collimator contour shape (line drawing data 29) displayed by copying on the positioning image 27 (step 216). The error in the amount of snout rotation (position deviation of the snout) can be calculated by one of two methods as in the case of calculating the position deviation of the patient 4 on the patient positioner 11. According to a first method, as described in the above embodiment with reference to FIGS. 7A and 7B, the error in the amount of snout rotation is calculated by using, as a reference region for the positioning, the line drawing data 29 which represents the planned collimator contour shape and is displayed by copying, and rotating the positioning image 27 so that the actual collimator contour shape 28 is matched with the planned collimator contour shape (line drawing data 29). According to a second method, as described in the above embodiment with reference to FIGS. 8A and 8B, the error in the amount of snout rotation is calculated by rotating the line drawing data 29, which represents the planned collimator contour shape and is displayed by copying, so that it is matched with the actual collimator contour shape 28.

The error in the amount of rotation of the snout 9 calculated by one of the above-described two methods is outputted from the positioning apparatus 7 to the snout controller 10 (step 217). The snout controller 10 having received the error in the amount of snout rotation automatically corrects the error in the amount of rotation of the snout 9 (step 218).

This embodiment can also reduce a variation in positioning accuracy caused depending on conditions of the positioning image, such as a contrast, thus enabling the positioning operation to be precisely performed in consideration of the positional relationship between the tumor position and the radiation field. It is hence possible to cut unwanted exposure of the patient to radiations, and to increase the efficiency of the positioning operations.

Further, the correction of the error in the amount of snout rotation can also be performed with automatic adjustment based on image recognition while reducing a variation depending on individual operators, improving reproducibility, and cutting the operations to be performed by the operator.

Note that the present invention is not limited to the above-described embodiments, and it can be practiced in various modification and applications. For example, with the above-described embodiments, in the positioning of the collimator 5, the reference image 26 and the positioning image 27 are both displayed on the monitor 13a for confirming the positional relationship between the line drawing data 29 representing the planned collimator contour shape and the tumor position. However, the reference image 26 is not necessarily required to be displayed. Stated another way, the positioning of the collimator 5 can also be performed in a similar manner to that described above by displaying only the positioning image 27 on the monitor 13a and displaying the line drawing data 29 in superimposed relation to the positioning image 27.

Also, with the above-described embodiments, in the positioning of the patient 4, the positioning operation using the positioning image captured in the direction of the irradiation beam is performed based on the line drawing data 29 representing the planned collimator contour shape, while the positioning operation using the positioning image captured in the direction forming an angle of 90° relative to the direction of the irradiation beam is performed using the other line drawing data representing, e.g., the organ shape, the bone shape, the body contour shape, or the clinical (or planning) target volume shape, instead of the planned collimator contour shape. However, the present invention is not limited to that scheme. Stated another way, in the positioning of the patient 4, the positioning operation using the positioning image captured in the direction of the irradiation beam may also be performed, as with the positioning image captured in the other direction, by using the line drawing data representing, e.g., the organ shape, the bone shape, the body contour shape, or the clinical (or planning) target volume shape, instead of the planned collimator contour shape. Such a modification can also provide similar advantages to those in the above-described embodiments.

Further, with the above-described embodiments, the snout drive unit 20 is connected to the snout controller 10 and the snout 9 is automatically controlled by the processing unit 13. However, the present invention may be modified such that the snout drive unit 20 is constituted as a manually-operated adjustment mechanism and the position of the snout 9 is manually adjusted in accordance with the error in the amount of rotation of the snout calculated from the positioning image 27.

What is claimed is:

1. A positioning system for radiation therapy, comprising a collimator for forming a radiation field, a snout in which is set said collimator, and a patient positioner for supporting a patient, wherein said positioning system further comprises:

a first display area for displaying a reference image as image information which is prepared during treatment planning and includes an affected part in a patient body;

a second display area for displaying a first positioning image as image information which is captured by X-ray equipment and includes the affected part in the patient body; and a processing control unit for displaying, on said reference image, figure data representing a planned collimator contour shape which is registered in the image information of said reference image during the treatment planning, displaying the figure data representing the planned collimator contour shape in said second display area, and producing positioning information of said patient positioner based on a figure representing the planned collimator contour shape, which is displayed in said second display area, and on said first positioning image displayed in said second display area.

2. The positioning system for the radiation therapy according to claim 1, farther comprising:
   a patient positioner drive unit for moving said patient positioner; and
   a patient positioner controller for controlling said patient positioner drive unit in accordance with the positioning information of said patient positioner, thereby moving said patient positioner.

3. The positioning system for the radiation therapy according to claim 1, further comprising:
   a third display area for displaying a second positioning image as image information, which is captured by X-ray equipment and includes an actual contour shape of said collimator; and
   said processing control unit displays said figure data representing the planned collimator contour shape in said third display area, and produces positioning information of said collimator based on the figure representing the planned collimator contour shape, which is displayed in said third display area, and on said second positioning image displayed in said third display area.

4. The positioning system for the radiation therapy according to claim 3, further comprising:
   a snout drive unit for rotating said snout in which is set said collimator; and
   a snout controller for controlling said snout drive unit in accordance with the positioning information of said collimator, thereby rotating said snout.

5. The positioning system for the radiation therapy according to claim 1, wherein said processing control unit displays said figure data representing the planned collimator contour shape at a center of said first display area, and displays said figure data representing the planned collimator contour shape by copying at a center of said second display area or said third display area.

6. A positioning method for radiation therapy employing a collimator for forming a radiation field, a snout in which is set said collimator, and a patient positioner for supporting a patient, wherein said positioning system comprises:
   a first step of displaying, in a first display area, a reference image as image information which is prepared during treatment planning and includes an affected part in a patient body, and displaying, in a second display area, a first positioning image as image information which is captured by X-ray equipment and includes the affected part in the patient body;
   a second step of displaying, on said reference image, figure clam representing a planned collimator contour shape which is registered in the image information of said reference image during the treatment planning, and displaying said figure data representing the planned collimator contour shape in said second display area; and
   a third step of producing positioning information of said patient positioner based on a figure representing the planned collimator contour shape, which is displayed in said second display area, and on said first positioning image displayed in said second display area.

7. The positioning method for the radiation therapy according to claim 6, further comprising:
   a fourth step of displaying, in a third display area, a second positioning image as image information, which is captured by X-ray equipment and includes an actual contour shape of said collimator;
   a fifth step of displaying said figure data representing the planned collimator contour shape in said third display area; and
   a sixth step of producing positioning information of said collimator based on the figure representing the planned collimator contour shape, which is displayed in said third display area, and on said second positioning image displayed in said third display area.

8. The positioning method for the radiation therapy according to claim 7, wherein, after executing said fourth to sixth steps to rotate said snout in accordance with the positioning information of said collimator for positioning of said collimator, said first to third steps are executed to move said patient positioner in accordance with positioning information of said patient positioner for positioning of said patient.

9. A positioning system for radiation therapy in which positioning of a patient and positioning of a collimator are performed prior to starting the radiation therapy, wherein said positioning system comprises:
   a patient positioner drive unit for moving a patient positioner supporting said patient;
   a snout drive unit for rotating about an irradiation beam axis a snout including said collimator set therein;
   an image capturing device for capturing an image of a contour shape of said collimator in an irradiating direction of a radiation;
   a display for displaying information of the captured image of said collimator in superimposed relation to figure data representing a collimator contour decided in treatment planning; and
   a processing control unit for producing first positioning information to control said snout drive unit such that said snout is rotated about the irradiation beam axis for the positioning of said collimator, and second positioning information to control said patient positioner drive unit such that said patient is moved for the positioning of said patient,
   wherein said processing control unit includes a collimator positioning apparatus for producing the first positioning information used for the positioning of said collimator based on collimator contour position information captured in the image information of said collimator and collimator contour position information provided by said figure data.

10. The positioning system for the radiation therapy according to claim 9, wherein said image capturing device captures the image of the collimator contour shape in a state where said collimator is set in said snout and said patient is not supported on said patient positioner.

11. The positioning system for the radiation therapy according to claim 10, further comprising:
   an input unit for moving the image information of said collimator which is displayed on said display,
   wherein said collimator positioning apparatus produces said first positioning information based on an amount of movement which is obtained when an operator moves the image information of said collimator by using said input unit such that the collimator contour contained in the image information of said collimator and the collimator contour provided by said figure data are matched with each other.

12. The positioning system for the radiation therapy according to claim 10, further comprising:
   an input unit for moving the figure data representing the collimator contour which is displayed on said display,
   wherein said collimator positioning apparatus produces said first positioning information based on an amount of movement which is obtained when an operator moves said figure data by using said input unit such that the collimator contour contained in the image information of said collimator and the collimator contour provided by said figure data are matched with each other.

13. The positioning system for the radiation therapy according to claim 11, further comprising a snout controller for controlling said snout drive unit in accordance with the first positioning information, thereby rotating said snout.

14. The positioning system for the radiation therapy according to claim 13, further comprising an image information storage for storing line-drawing image information that is obtained by registering said figure data in the image information of said collimator.

15. The positioning system for the radiation therapy according to claim 9, further comprising:
a display for displaying first figure data and second figure data, each of which is the figure data representing the collimator contour decided in treatment planning, in superimposed relation to first image information given as image information including an affected pan in a patient body and captured by X-ray equipment and second image information given as image information including an affected pan in the patient body which is prepared during the treatment planning, respectively,
wherein said processing control unit includes a patient positioning apparatus for producing said second positioning information used for the positioning of said patient based on relative position information of said first figure data relative to said first image information and relative position information of said second figure data relative to said second image information.

16. The positioning system for the radiation therapy according to claim 15, further comprising:
an input unit for moving said second image information displayed on said display,
wherein said patient positioning apparatus produces said second positioning information based on an amount of movement which is obtained when an operator moves said second image information by using said input unit such that a relative positional relationship between said second figure data and said second image information is identical to a relative positional relationship between said first figure data and said first image information.

17. The positioning system for the radiation therapy according to claim 15, further comprising:
an input unit for moving said second figure data displayed on said display,
wherein said patient positioning apparatus produces positioning information of said patient based on an amount of movement which is obtained when an operator moves said second figure data by using said input unit such that a relative positional relationship between said second figure data and said second image information is identical to a relative positional relationship between said first figure data and said first image information.

18. The positioning system for the radiation therapy according to claim 16, further comprising a patient positioner controller for controlling said patient positioner drive unit in accordance with the second positioning information, thereby moving said patient positioner.

19. The positioning system for the radiation therapy according to claim 18, further comprising an image information storage for storing at least one of two kinds of line-drawing image information which are obtained by registering said first figure data and said second figure data in said first image information and said second image information, respectively.

20. A positioning method for radiation therapy in which positioning of a patient and positioning of a collimator are performed prior to starting the radiation therapy,
wherein the positioning of said patient is performed by moving a patient positioner for supporting said patient after the positioning of said collimator has been performed by rotating about an irradiation beam axis a snout including said collimator set therein.

21. The positioning method for the radiation therapy according to claim 20, further comprising the steps of:
capturing an image of a contour shape of said collimator in an irradiating direction of a radiation in a state where said collimator is set in said snout and said patient is not supported on said patient positioner;
displaying information of the captured image of said collimator in superimposed relation to figure data representing a collimator contour decided in treatment planning; and
performing the positioning of said collimator based on collimator contour position information captured in the image information of said collimator and collimator contour position information provided by said figure data.

22. The positioning method for the radiation therapy according to claim 20, further comprising the steps of:
supporting said patient on said patient positioner and capturing an image of an area including an affected part in a patient body by X-ray equipment; and
displaying first figure data and second figure data, each of which represents the collimator contour decided in the treatment planning, in superimposed relation to first image information given as image information including the captured affected part in the patient body and second image information given as image information including an affected part in the patient body which is prepared during the treatment planning, respectively; and
performing the positioning of said patient based on relative position information of said first figure data relative to said first image information and relative position information of said second figure data relative to said second image information.

23. A positioning system for radiation therapy, comprising a collimator for forming a radiation field, a snout in which is set said collimator, and a patient positioner for supporting a patient, wherein said positioning system further comprises:
a first display area for displaying a reference image as image information which is prepared during treatment planning and includes an affected part in a patient body;
a second display area for displaying a first positioning image as image information which is captured by X-ray equipment and includes the affected pan in the patient body, said first image information including image information of an isocenter position; and
a processing control unit for displaying, on said reference image, figure data representing a planned collimator contour shape which is registered in the image information of said reference image during the treatment planning, displaying said figure data representing the planned collimator contour shape by copying at a position corresponding to the isocenter position in said second display area in which said first image information is displayed, and producing positioning information of said patient positioner based on an amount of relative movement between said figure data representing the planned collimator contour shape and the image information of said first positioning image. The amount of said relative movement being by moving The image information of said first positioning image relative to said figure data representing the planned collimator contour shape in said second display area such that the affected part in the patient body captured in said first positioning image falls within the planned collimator contour shape represented by said figure data.

24. A positioning method for radiation therapy employing a collimator for forming a radiation field, a snout in which is set said collimator, and a patient positioner for supporting a patient, wherein said positioning method comprises:

a first step of displaying, in a first display area, a reference image as image information which is prepared during treatment planning and includes an affected part in a patient body, and displaying, in a second display area, a first positioning image as image information which is captured by X-ray equipment and includes the affected part in the patient body, said first image information including image information of an isocenter position;

a second step of displaying, on said reference image, figure data representing a planned collimator contour shape which is registered in the image information of said reference image during the treatment planning, and displaying said figure data representing the planned collimator contour shape by copying at a position corresponding to the isocenter position in said second display area in which said first image information is displayed;

a third step of, based on said reference image and said first positioning image, moving the image information of said first positioning image relative to said figure data representing the planned collimator contour shape in said second display area such that the affected part in the patient body captured in said first positioning image falls within the planned collimator contour shape represented by said figure data; and a fourth step of producing positioning information of said patient positioner based on an amount of relative movement between said figure data representing the planned collimator contour shape and the image information of said first positioning image.

* * * * *